(12) United States Patent
Daines

(10) Patent No.: US 11,207,241 B2
(45) Date of Patent: Dec. 28, 2021

(54) PREFILLED MEDICATION DEVICE, METHOD OF MAKING AND USING THE SAME

(71) Applicant: PHD Preventative Health Care and Diagnostics, Inc., Colorado Springs, CO (US)

(72) Inventor: Eric R. Daines, Colorado Springs, CO (US)

(*) Notice: Subject to any disclaimer, the term of this patent is extended or adjusted under 35 U.S.C. 154(b) by 0 days.

(21) Appl. No.: 14/775,714

(22) PCT Filed: Mar. 17, 2014

(86) PCT No.: PCT/US2014/030756
§ 371 (c)(1),
(2) Date: Sep. 13, 2015

(87) PCT Pub. No.: WO2014/145906
PCT Pub. Date: Sep. 18, 2014

(65) Prior Publication Data
US 2016/0022539 A1    Jan. 28, 2016

Related U.S. Application Data

(60) Provisional application No. 61/798,328, filed on Mar. 15, 2013.

(51) Int. Cl.
*A61J 1/20* (2006.01)
*A61M 5/315* (2006.01)
(Continued)

(52) U.S. Cl.
CPC ............. *A61J 1/2096* (2013.01); *A61K 39/35* (2013.01); *A61M 5/178* (2013.01); *A61M 5/30* (2013.01);
(Continued)

(58) Field of Classification Search
CPC .......... A61J 1/209; A61J 1/2096; A61M 5/30; A61M 5/24; A61M 2005/3131; A61M 5/178; A61M 5/31511; A61K 39/35
See application file for complete search history.

(56) References Cited

U.S. PATENT DOCUMENTS

| 4,740,371 A | * | 4/1988 | St. Remy | A61K 39/35 |
|---|---|---|---|---|
| | | | | 424/171.1 |
| 4,936,833 A | | 6/1990 | Sams | |

(Continued)

FOREIGN PATENT DOCUMENTS

| WO | 2001/032208 | 5/2001 |
|---|---|---|
| WO | 2009/012601 | 1/2009 |

(Continued)

OTHER PUBLICATIONS

Nanda, et al. "Dose dependence and time course of the immunologic response to administration of standardized cat allergen extract". 2004. American Academy of Allergy, Asthma and Immunology. vol. 114:1339-44.*

(Continued)

*Primary Examiner* — Theodore J Stigell
(74) *Attorney, Agent, or Firm* — Scott J. Hawranek

(57) ABSTRACT

The invention generally relates to prefilled disposable medication devices, method of making, and using to store, contain and deliver at least a diluent for allergenic extract and more particularly to a prefilled cartridge containing a diluent for allergenic extract for use with an injection pen for allergy treatments.

15 Claims, 4 Drawing Sheets

(51) Int. Cl.
*A61K 39/35* (2006.01)
*A61M 5/178* (2006.01)
*A61M 5/30* (2006.01)
*A61M 5/24* (2006.01)
*A61M 5/31* (2006.01)

(52) U.S. Cl.
CPC .......... *A61M 5/31511* (2013.01); *A61M 5/24* (2013.01); *A61M 2005/3131* (2013.01); *A61M 2205/3368* (2013.01); *A61M 2205/587* (2013.01); *A61M 2205/6054* (2013.01); *A61M 2205/6081* (2013.01); *A61M 2205/8206* (2013.01); *A61M 2205/8243* (2013.01)

(56) References Cited

U.S. PATENT DOCUMENTS

| | | |
|---|---|---|
| 5,104,380 A | 4/1992 | Holman et al. |
| 5,211,285 A | 5/1993 | Haber et al. |
| 5,334,162 A | 8/1994 | Harris |
| 5,454,786 A | 10/1995 | Harris |
| 5,725,500 A | 3/1998 | Micheler |
| 5,733,258 A | 3/1998 | Lane |
| 5,879,163 A | 3/1999 | Brown et al. |
| 5,961,332 A | 10/1999 | Joao |
| 6,264,629 B1 | 7/2001 | Landau |
| 6,443,942 B2 | 9/2002 | Van Antwerp et al. |
| 6,461,334 B1 | 10/2002 | Buch Rasmussen et al. |
| 7,104,973 B2 | 9/2006 | Woolston et al. |
| 7,547,293 B2 | 6/2009 | Williamson et al. |
| 7,618,393 B2 | 11/2009 | Bingham et al. |
| 7,654,995 B2 | 2/2010 | Warren et al. |
| 7,678,073 B2 | 3/2010 | Griffiths et al. |
| 7,699,802 B2 | 4/2010 | Steinway et al. |
| 7,765,111 B2 | 7/2010 | Brown |
| 7,850,663 B2 | 12/2010 | Sullivan et al. |
| 7,899,528 B2 | 3/2011 | Miller et al. |
| 8,015,030 B2 | 9/2011 | Brown |
| 8,167,835 B2 | 5/2012 | Keller |
| 8,267,913 B2 | 9/2012 | Fangrow |
| 8,529,500 B2 | 9/2013 | Bingham et al. |
| 2002/0045154 A1 | 4/2002 | Wood et al. |
| 2002/0061315 A1 | 5/2002 | Kundig et al. |
| 2002/0193740 A1* | 12/2002 | Alchas ............... A61M 5/158 604/117 |
| 2003/0017440 A1 | 1/2003 | Bergey et al. |
| 2003/0168868 A1 | 9/2003 | Bierlein |
| 2003/0199071 A1* | 10/2003 | Langermann ........ C07K 14/245 435/200 |
| 2004/0176728 A1 | 9/2004 | Fisher et al. |
| 2004/0186432 A1* | 9/2004 | Barry ............... A61M 5/30 604/152 |
| 2005/0000514 A1* | 1/2005 | Sullivan ........... A61M 15/0028 128/200.24 |
| 2005/0038386 A1 | 2/2005 | Fago et al. |
| 2005/0071197 A1 | 3/2005 | Goldberg |
| 2005/0124941 A1 | 6/2005 | Panchula et al. |
| 2005/0232930 A1 | 10/2005 | Richter-Friss et al. |
| 2007/0027428 A1 | 2/2007 | Bingham |
| 2007/0239112 A1 | 10/2007 | Fago et al. |
| 2008/0027007 A1 | 1/2008 | Benner et al. |
| 2008/0144896 A1 | 6/2008 | Burke |
| 2010/0290792 A1 | 11/2010 | Tsuchida |
| 2011/0313395 A1 | 12/2011 | Krulevitch et al. |
| 2012/0000592 A1 | 1/2012 | Mase et al. |
| 2012/0220640 A1 | 8/2012 | Ashdown et al. |
| 2012/0229624 A1 | 9/2012 | Calman et al. |
| 2012/0230557 A1 | 9/2012 | Calman et al. |
| 2012/0277684 A1 | 11/2012 | Cronenberg et al. |
| 2012/0310943 A1 | 12/2012 | Palestrant et al. |
| 2013/0035634 A1 | 2/2013 | Cappello et al. |
| 2013/0150820 A1 | 6/2013 | Cappello et al. |
| 2014/0005632 A1 | 1/2014 | Bingham et al. |
| 2014/0290792 A1* | 10/2014 | Avery ............... A61M 5/24 141/18 |

FOREIGN PATENT DOCUMENTS

| | | |
|---|---|---|
| WO | 2010/151704 | 12/2010 |
| WO | WO 2014/145906 | 9/2014 |

OTHER PUBLICATIONS

Nanda et al. "Dose dependence and time course of the immunologic response to administration of standardized cat allergen extract," Journal of Allergy and Clinical Immunology, vol. 114, No. 6, Dec. 2004, pp. 1339-1344.

International Search Report for International (PCT) Patent Application No. PCT/US14/30756, dated Sep. 8, 2014, 3 pgs.

Written Opinion for International (PCT) Patent Application No. PCT/US14/30756, dated Sep. 8, 2014, 21 pgs.

Kubick, "An Uncertain Future: The Impact of Medical Process and Diagnostic Method Patents on Healthcare in the United States," Northwestern Journal of Technology and Intellectual Property, vol. 9, Issue 3, Article 8, 2010.

Nelson, et al., "Allergen Immunotherapy Extract Preperation Manual," Chapter 9, AAAAI Practice Management Resource Guide, 2012 edition; 39 pages.

International Preliminary Report on Patentability for International (PCT) Patent Application No. PCT/US/2014/030756, dated Sep. 15, 2015, 22 pages.

Keet, et al., "The safety and efficacy of sublingual and oral immunotherapy for milk allergy," J Allergy Clin Immunol, vol. 129, No. 2, 2011.

* cited by examiner

PREFILLED MEDICATION DEVICE, METHOD OF MAKING AND USING THE SAME

The present application is a National Stage of International Application No. PCT/US2014/030756, filed Mar. 17, 2014, which claims the benefit of U.S. Provisional Patent Application No. 61/798,328 filed on Mar. 15, 2013, each of which is fully incorporated herein by reference.

BACKGROUND OF THE INVENTION

Field of the Invention

The invention generally relates to a prefilled disposable medical device that is used to store, contain and deliver at least a diluent for an allergenic extract and more particularly to a prefilled cartridge containing a diluent for an allergenic extract and/or an allergenic extract for use with an injection device for allergy treatments.

SUMMARY OF THE INVENTION

Accordingly, the invention is directed to hermetic packaging and a method of forming the same that substantially obviates one or more of the problems due to limitations and disadvantages of the related art.

An advantage of the invention is a device that provides a more convenient solution for a patient to self-administer an allergy treatment.

Another advantage of the invention is a device that substantially decreases the chance of dosing errors.

Yet another advantage of the invention is a device that is labeled with a label, e.g., an RFID label, that is machine readable either optically, wirelessly and the like.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, a prefilled cartridge for use with an injection device includes a container having a first end, configured to receive a cap, and an open second end. A piston is configured to be arranged within an interior portion of the container though the open second end. The piston is operable to move from a first position to a second position, e.g., upon operation of an injection device the piston moves from a first position to a second position. A cap including a color code indicative of a predetermined concentration of at least one antigen is configured on one end of the cartridge. The prefilled cartridge includes one or more of a diluent for an allergenic extract, an allergenic extract and combinations of the same.

One embodiment is directed towards a prefilled cartridge for use with an injection device. The prefilled cartridge is configured to work with an injection device that is needle free or includes a needle. Any injection device configured to receive a cartridge may be utilized. The injection device may have a pen type shape and these devices are known in the art and described herein. In the embodiment, the prefilled cartridge includes a container having a first end configured to receive a cap and an open second end and a piston or plunger configured to be arranged within an interior portion of the container.

In one embodiment, the piston or plunger is operable to move from a first position to a second position, e.g., upon operation of an injection device when the cartridge is operably positioned within the injection device. This action of the injection device may be achieved by a mechanical action, electronic action, pneumatic action, magnetic action, air pressure action and combinations of the same. That is, a piston moves from a first position to a second position to engage with the piston or plunger of the prefilled cartridge.

The cartridge can also include a cap or other portion having a color code indicative of a predetermined concentration of at least one antigen contained within the cartridge. The cap also includes a seal, e.g., a self-healing seal permitting a needle or other device to puncture the seal and allowing it to be resealed upon the needle or other device.

One embodiment is directed towards a method of preparing an allergen extract for an immunotherapy treatment with a prefilled cartridge for use with an injection device. The method includes providing a first prefilled cartridge for use with the injection device, the prefilled cartridge includes a container having a first end configured to receive a cap and an open second end, a piston arranged within an interior portion of the container where the piston is operable to move from a first position to a second position, and a solution contained between the piston and the first end, the solution including a diluent for an allergenic extract. The method further includes adding at least one allergen extract to the prefilled cartridge to form the allergen extract for an immunotherapy treatment at first concentration. Optionally, additional steps may be performed to by adding a predetermined amount of the allergen extract at a first concentration in the prefilled cartridge to a second prefilled cartridge to form an allergen extract for an immunotherapy treatment at a second concentration.

One embodiment is directed towards a method of preparing an allergen extract for an immunotherapy treatment with a prefilled cartridge for use with an injection device. The method includes providing a prefilled cartridge including a solution having a diluent for an allergenic extract. Next, combining one or more allergenic extracts into a first container to form an allergenic extract concentrate and obtaining a predetermined volume of diluent in the prefilled cartridge. Next, forming an allergen extract for an immunotherapy treatment at a first concentration by combining a predetermined volume of the concentrate into the prefilled cartridge. Optionally, additional steps may be performed to by adding a predetermined amount of the allergen extract at a first concentration in the prefilled cartridge to a second prefilled cartridge to form an allergen extract for an immunotherapy treatment at a second concentration.

One embodiment is directed towards a method of preparing an allergen extract for immunotherapy treatment cartridge for use with an injection device. The method includes providing a prefilled cartridge containing where the prefilled cartridge is empty of any liquid. Next, combining one or more allergenic extract into a first container to form an allergenic extract concentrate and obtaining a predetermined volume of diluent in the prefilled cartridge. Next, forming the allergen extract for immunotherapy treatment by combining a predetermined volume of the concentrate into the prefilled cartridge. Optionally, additional steps may be performed to by adding a predetermined amount of the allergen extract at a first concentration in the prefilled cartridge to a second prefilled cartridge to form an allergen extract for an immunotherapy treatment at a second concentration.

One embodiment is directed towards a method of administering immunotherapy to a patient with an injection device and prefilled cartridge. The method includes providing the injection device and loading the prefilled cartridge into the injection device. The prefilled cartridge includes an efficacious amount of allergen extract for immunotherapy. Next, the injection is operated at a treatment situs of the patient to administer an efficacious dosage of the allergen extract.

One embodiment is directed towards a medical kit for immunotherapy. The medical kit may include an injection device and one or more prefilled cartridges include an allergen extract for immunotherapy and instructions for use. Optionally or alternatively, the medical kit for immunotherapy includes one or more prefilled cartridges comprising an allergen extract for immunotherapy or diluent without the allergen extract for immunotherapy.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
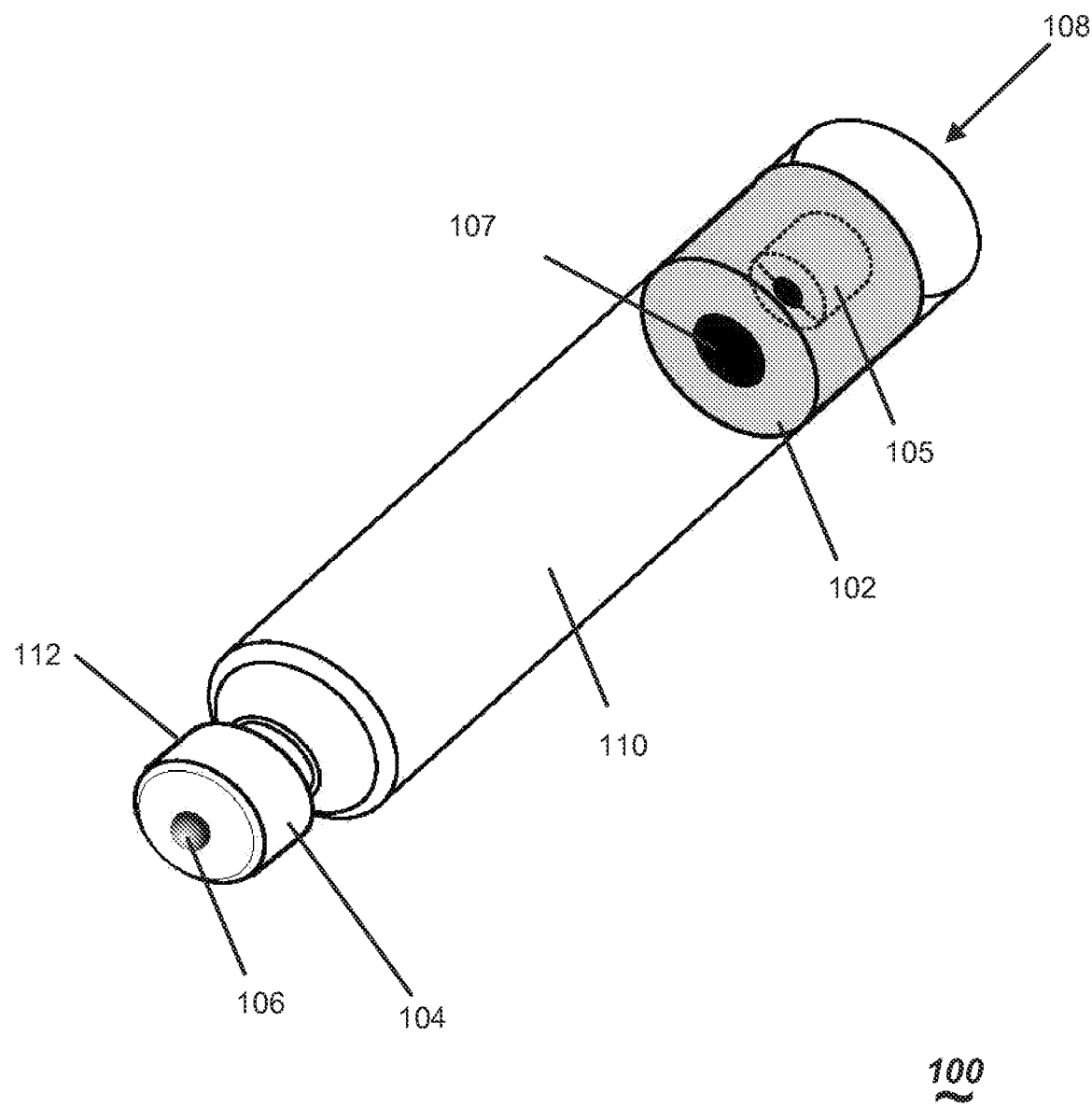
FIG. 1 illustrates a perspective view of a prefilled cartridge.

For the purposes of promoting an understanding of the principles of the present disclosure, reference will now be made to the exemplary embodiments illustrated in the drawing(s), and specific language will be used to describe the same.

Appearances of the phrases an "embodiment," an "example," or similar language in this specification may, but do not necessarily, refer to the same embodiment, to different embodiments, or to one or more of the figures. The features, functions, and the like described herein are considered to be able to be combined in whole or in part with one another as the claims and/or art may direct, either directly or indirectly, implicitly or explicitly.

As used herein, "comprising," "including," "containing," "is," "are," "characterized by," and grammatical equivalents thereof are inclusive or open-ended terms that do not exclude additional unrecited elements or method steps unless explicitly stated otherwise.

In order to more fully appreciate the present disclosure and to provide additional related features, each of the following references are incorporated herein by reference in their entirety:

(1) U.S. Pat. No. 4,936,833 by Sams which discloses a cartridge assembly for a syringe-type medication dispensing unit including a cartridge having a cartridge body with first and second ends. A pierceable membrane is mounted at the first end and a piston is mounted at the second end, with a volume of medication contained in the cartridge body between the membrane and the piston. A cartridge holder receives the cartridge and defines first and second ends. The first holder end defines a central opening and an external thread for mounting a double-ended needle. The second holder end defines an external thread for securing the holder to a medication dispensing unit and an actuating shoulder. The holder frictionally engages the cartridge to form an assembly which can be handled as a single modular unit with the cartridge held securely in the holder by frictional engagement.

(2) U.S. Pat. No. 5,104,380 by Holman, et al., which discloses a generally pen-like syringe incorporating a dose metering device provided by a cap rotatable with respect to a pen body to a position related to the dose of medicament (for example insulin) to be injected. The rotation compresses a coil spring, which is prevented from unwinding by cooperating ratchet teeth. When the dose is to be injected, a trigger slide is moved to the left causing the ratchet teeth to come out of engagement. This permits the spring to unwind, thereby rotating a drive sleeve, drive gear and a drive plunger. The drive plunger is formed with a quick pitch screw thread so that its rotational movement is accompanied by axial movement to cause medicament to be discharged from a cartridge and injected through a needle.

(3) U.S. Pat. No. 5,211,285 by Haber, et al. which discloses a telescoping, pharmaceutical mixing container including outer and inner containers telescopically mounted to one another with the inner end of the inner container situated within the outer container. The inner container has a piston cap mounted to it so as to provide a piston-like seal between the inner and outer containers, and houses a piston within its interior. The piston cap defines a flow path between first and second variable volume regions within the inner and outer containers respectively. Reciprocating the inner container within the outer container causes the pharmaceutical to pass through the flow path and between the variable volume regions and mix. The mixing container is preferably used with a metering assembly including a metering stop, threadably positionable along the axis of the mixing container, and a driver secured to the inner container. The driver includes a drive stop which engages the metering stop once the inner container has moved an appropriate distance towards its collapsed condition, typically during an injection.

(4) U.S. Pat. No. 5,334,162 by Harris which discloses a cartridge assembly for holding a lyophilized product, forming a disposable portion of a pen injector including a cylindrical glass cartridge adapted to receive the product, a closure cap, a cartridge case, and a plunger mechanism. The closure cap is adapted to retain an elastomeric disc seal during lyophilization and includes diametrically opposed ledges. The closure cap and seal are adapted to cover a neck portion of the ampule, the neck portion having on its end a radially extending circumferential flange. The ledges of the closure cap and the flange of the neck portion allow the closure cap to remain open during lyophilization, oxygen purge and nitrogen overlay. An oval-shaped indentation formed on the inside of the closure cap aids in snapping the closure cap about the flange without crimping to retain the closure cap underneath the flange. Reconstitution of the lyophilized drug is accomplished without foaming by use of an obliquely angled connector which causes the diluent to indirectly impinge on the drug. The injection device and cartridge assembly cooperate such that the length of travel of the plunger rod during retraction is less than the axial length of a recess in the rod tip.

(5) U.S. Pat. No. 5,454,786 by Harris which discloses a cartridge assembly for holding a lyophilized product, forming a disposable portion of a pen injector including a cylindrical glass cartridge adapted to receive the product, a closure cap, a cartridge case, and a plunger mechanism. The closure cap is adapted to retain an elastomeric disc seal during lyophilization and includes diametrically opposed ledges. The closure cap and seal are adapted to cover a neck portion of the ampule, the neck portion having on its end a radially extending circumferential flange. The ledges of the closure cap and the flange of the neck portion allow the closure cap to remain open during lyophilization, oxygen purge and nitrogen overlay. An oval-shaped indentation formed on the inside of the closure cap aids in snapping the closure cap about the flange without crimping to retain the closure cap underneath the flange. Reconstitution of the lyophilized drug is accomplished without foaming by use of an obliquely angled connector which causes the diluent to indirectly impinge on the drug. The injection device and cartridge assembly cooperate such that the length of travel of the plunger rod during retraction is less than the axial length of a recess in the rod tip.

(6) U.S. Pat. No. 5,725,500 by Micheler which discloses a container for a liquid medicament suspension, e.g. an insulin crystal suspension, having a tube with a sealing piston, a cap, and a mixing element which moves along the tube to assist mixing the suspension. The element is guided by the inner surface of the tube and has restricted lateral movement but is free to move axially, for example, by tilting or end to end inversion of the container. Flow passages such as apertures and peripheral recesses are provided in the mixing element which can serve to promote turbulent flow. The containers are particularly suited for use as multi-dose cartridges for pen-like injection devices or for portable infusion devices which have piston-operating mechanisms to cooperate with the container piston.

(7) U.S. Pat. No. 5,733,258 by Lane which discloses a closed system for the handling of injectable biological products and vaccines used in the treatment and prevention of livestock diseases. This system embodies a prefilled disposable cartridge with a disposable needle attached and a metered pistol grip syringe. The cartridge is breech loaded into the syringe and the product is dispensed from the cartridge by a unique drag link mechanism as a means for advancing the plunger rod (36) and forcing the vaccine from the cartridge into the flesh of the animal being treated. Each prefilled cartridge is disposed of after it is emptied and no cleaning is required. A color coding system between the prefilled cartridges and the syringe bodies insures that proper dosages are given and that different products are not mixed up or confused with each other by the technicians dispensing the biological products.

(8) U.S. Pat. No. 6,264,629 by Landau, which discloses a gas-powered, single-use, needle-less hypodermic jet injection device including a hand-held injector, and a drug injection cartridge which provides a cylinder of liquid medication to be injected, an injection orifice, and an injection piston. Forceful movement of the injection piston in the cylinder causes an injection jet of medication to be expelled from the injection orifice. The injection device also includes a hermetically sealed gas pressure capsule which remains sealed until the moment of injection and powers the jet injection after opening of this cartridge.

(9) U.S. Pat. No. 6,443,942 by Van Antwerp, et al., which discloses medical devices such as medication infusion pumps having internal surfaces that are treated to inhibit protein denaturation. In accordance with the invention, hydrophilic internal surfaces and related coating methods are provided to reduce or eliminate accumulation of medication deposits which can otherwise occur when handling complex protein-based medications. Preferred hydrophilic pump surfaces include hydrophilic surfactants (PEO) or (PEG) coatings which exhibit very low protein adsorption characteristics. Several methods are disclosed for producing such treated surfaces including the covalent attachment of hydrophilic surfactants.

(10) U.S. Pat. No. 7,104,973 by Woolston, et al. which discloses an apparatus for patients having diabetes who take a combination of slow and fast acting types of insulin. It is important that the different forms of medicament do not become confused and that the patient does not receive the incorrect medicament. In combination, a medicament delivery apparatus and a medicament cartridge are provided, the medicament delivery apparatus including at least one switch and the medicament cartridge comprising a cartridge housing within which a medicament is provided, a displaceable piston located internally at one end of the housing and a raised ring of material about an external periphery of the medicament cartridge, the ring of material being of sufficient dimensions, in use, to trip the at least one switch of the medicament delivery apparatus.

(11) U.S. Pat. No. 7,547,293 by Williamson, et al. which discloses a needle-free hypodermic jet injection device having an actuation system to effect an injection from a drug delivery system. The actuation system includes an injection force assembly adapted to transmit a driving force to the drug delivery system. The actuation system further includes a trigger assembly adapted to alter the actuation system between a plurality of configurations including a fired configuration in which the injection force assembly transmits a driving force to the drug delivery system. In some embodiments, the device has a recoil restriction system including a restriction member adapted to couple the recoil restriction system to the trigger assembly and a recoil member coupled to the injection force assembly and movable relative to the restriction member. The restriction member limits movement of the recoil member once the recoil member moves a predetermined distance relative to the restriction member.

(12) U.S. Pat. No. 7,618,393 by Bingham, et al., which discloses a needle-less injector device for delivering a dose of fluid intradermally, subcutaneously or intramuscularly to an animal or human. The device includes an inner housing having opposed ends. A syringe is disposed in one end of the inner housing. The syringe includes a nozzle for delivering a dose of fluid held within the syringe. A plunger is movably disposed within the syringe. A spring powered hammer is movably disposed within the inner housing. The hammer cooperates with the plunger to drive the dose of medicament from the nozzle. An injection delivery spring for powering the hammer is positioned and compressed between the other end of the inner housing and the spring powered hammer. An outer housing slideably supports the inner housing. A skin tensioning spring is mounted between the inner housing and the outer housing, the skin tensioning spring biasing the nozzle of the syringe against the animal or human. A trigger mechanism is disposed in the outer housing, the trigger mechanism cooperating with the spring powered hammer to release the injection delivery spring, wherein the size of the injection delivery spring and the length of the hammer dictate the amount of dose delivered and whether the dose is delivered intradermally, subcutaneously or intramuscularly to an animal or human.

(13) U.S. Pat. No. 7,654,995 by Warren, et al. which discloses a vial adaptor for removing liquid contents from a vial including a piercing member and a bag. The bag can be contained within the piercing member such that the bag is introduced to the vial when the vial adaptor is coupled with the vial. In some embodiments, the bag expands within the vial as liquid is removed from the vial via the adaptor, thereby regulating pressure within the vial. In other embodiments, a vial comprises a bag for regulating pressure within the vial as liquid is removed therefrom. In some embodiments, a vial adaptor is coupled with the vial in order to remove the liquid. In some embodiments, as the liquid is removed from the vial via the adaptor, the bag expands within the vial, and in other embodiments, the bag contracts within the vial.

(14) U.S. Pat. No. 7,678,073 by Griffiths, et al. which discloses an automatic injector that separately stores liquid and dry components in respective compartments. When the injector is activated, a fluid-directing member between the liquid and dry compartments causes the liquid component to form a vortex as the liquid flows into the dry compartment. This allows the two components to combine more thoroughly and quickly to form a liquid solution that is delivered to an injection site.

(15) U.S. Pat. No. 7,699,802 by Steinway, et al., which discloses a needle-less injector device that includes an outer housing and an inner housing that is slideably supported from the outer housing is disclosed. The inner housing supporting a vial that includes a nozzle for delivering a fluid held within the vial. A spring powered ram that is adapted for pushing a seal and plunger is mounted within inner housing. A skin tensioning spring mounted between the inner housing and the outer housing is used for pushing the leading end of the inner housing away from the outer housing. A trigger that cooperates with the spring-powered ram is used to release the ram from the cocked position only when the inner housing is in a firing position.

(16) U.S. Pat. No. 7,850,663 by Sullivan, et al. which discloses a method and device for intradermal delivery of a reconstituted powdered medicament. The device includes a chamber, which is in fluid communication with a microdevice, e.g. microabrader or one or more microneedles. A cartridge containing the powdered medicament may be located within said chamber. At least one burstable membrane retains a powdered medicament within the housing. The method involves the steps of positioning the device at a delivery site on the skin of a patient and intradermally administering the medicament by dispensing a diluent from a diluent source through an inlet port to rupture the membranes, reconstitute the powdered medicament and deliver the reconstituted medicament through the microdevice to the dermal region of the skin.

(17) U.S. Pat. No. 7,899,528 by Miller, et al. which discloses an automatic external defibrillator apparatus which may be provided for use in cooperation with an intraosseous apparatus. Apparatus and methods may also be provided to execute protocols calling for external defibrillation and drug delivery. The disclosure provides a medical apparatus including two electrodes, a processor, a display, a driver, a drug delivery slot, a drug delivery port, and a voltage source. The two electrodes may include an attachment operable to releasably connect the two electrodes to the patient. The processor may be operable to collect and analyze a rhythm associated with the patient's heart from the two electrodes. The display may be operable to communicate instructions to a user. The driver may be operable to insert an intraosseous device into a bone and associated bone marrow of the patient. The drug delivery slot may be operable to receive a drug. The drug delivery port may be operable to communicate the drug from the drug delivery slot to the patient via the intraosseous device. The voltage source may be operable to deliver an electric shock to the patient via the two electrodes.

(18) U.S. Pat. No. 8,167,835 by Keller which discloses a single chamber device for drawing in and dispensing components comprising a syringe housing, a piston that is actuatable by a plunger unit, and a mixing assembly whose rod is guided through the piston and operatively connected to the plunger unit. The plunger unit comprises a plunger rod that is articulated at the mixing rod and provided with means that are engageable with the mixing rod. In this manner, a mixture of different components, particularly also bone cement, can be both created and dispensed in a simple and inexpensive single chamber device.

(19) U.S. Pat. No. 8,267,913 by Fangrow which discloses a vial adaptor for removing liquid contents from a vial including a piercing member and a bag. The bag can be contained within the piercing member such that the bag is introduced to the vial when the vial adaptor is coupled with the vial. In some embodiments, the bag expands within the vial as liquid is removed from the vial via the adaptor, thereby regulating pressure within the vial. In other embodiments, a vial comprises a bag for regulating pressure within the vial as liquid is removed therefrom. In some embodiments, a vial adaptor is coupled with the vial in order to remove the liquid. In some embodiments, as the liquid is removed from the vial via the adaptor, the bag expands within the vial, and in other embodiments, the bag contracts within the vial.

(20) U.S. Pat. No. 8,529,500 by Bingham, et al., which discloses a needle-less injector device for delivering a dose of fluid intradermally, subcutaneously or intramuscularly to an animal or human. The device includes an inner housing having opposed ends. A syringe is disposed in one end of the inner housing. The syringe includes a nozzle for delivering a dose of fluid held within the syringe. A plunger is movably disposed within the syringe. A spring powered hammer is movably disposed within the inner housing. The hammer cooperates with the plunger to drive the dose of medicament from the nozzle. An injection delivery spring for powering the hammer is positioned and compressed between the other end of the inner housing and the spring powered hammer. An outer housing slideably supports the inner housing. A skin tensioning spring is mounted between the inner housing and the outer housing, the skin tensioning spring biasing the nozzle of the syringe against the animal or human. A trigger mechanism is disposed in the outer housing, the trigger mechanism cooperating with the spring powered hammer to release the injection delivery spring, wherein the size of the injection delivery spring and the length of the hammer dictate the amount of dose delivered and whether the dose is delivered intradermally, subcutaneously or intramuscularly to an animal or human.

(21) U.S. Patent Application Publication No. 2004/0176728 by Fischer, et al. which discloses a prefilled injection apparatus for multiple dosings of medication. The protective housing element into which is installed the mechanical drive mechanism used to force the medication from the apparatus extends forward to provide a volume in which is directly contained a multi-dose quantity of medicine, and the medicine is sealed between a movable piston and a septum each in fluid tight engagement with the protective housing element. This design advantageously eliminates the need for using a separate cartridge within the apparatus. A method of making a cartridge-free, multi-dose injection apparatus is also disclosed.

(22) U.S. Patent Application Publication No. 2005/0124941 by Panchula, et al., which discloses cartridges provided for storing and facilitating the delivery of pharmaceutical formulations. In one preferred embodiment, the cartridge comprises a body including a bore extending through the body, and a plunger movably disposed in the bore. The bore has a transverse dimension at a distal end that is equivalent to that at a midpoint. The plunger has a planar contact surface that is transversely coextensive with the bore for applying a force to a pharmaceutical formulation contained in the bore. This configuration helps to eliminate dead volume, and therefore enables filing by volume rather than weight to ensure accurate dosing.

(23) U.S. Patent Application Publication No. 2007/0027428 by Bingham, et al., which discloses a needle-free or needle-less intradermal injection device that is capable of delivering an agent of interest to only the intradermal space. The intradermal device can deliver lower volumes of an agent than commonly used with present devices. In one aspect of the invention, the intradermal device is useful for delivering one or more agents to the intradermal space for eliciting immune responses particular to the dermal layer. In other aspects of the invention, the intradermal device is useful for delivering one or more agents to the intradermal space for treating, delaying development of delaying the progression of preventing, and/or ameliorating symptoms of various diseases, disease states, and conditions.

(24) U.S. Patent Application Publication No. 2008/0027007 by Benner, et al. which discloses drug development against acute radiation injury caused by exposure to high-energy electromagnetic waves (X-rays, gamma rays) or particles (alpha particles, beta particles, neutrons). To date, there is no effective drug to ameliorate radiation injury after accidental exposure to ionizing irradiation. The invention provides a method of treating radiation injury of a subject in need thereof comprising administering to the subject a peptide, or functional analogue or derivative thereof, of smaller than 30 amino acids. Furthermore, the invention provides use of a peptide, or functional analogue or derivative thereof, of smaller than 30 amino acids for the production of a pharmaceutical composition for the treatment of a subject suffering from or believed to be suffering from radiation injury. In particular, the invention provides anti-radiation peptides having a dose reduction factor (DRF) against acute gamma irradiation of at least 1.10, said DRF determinable by testing which dose of radiation results in 50% mortality at 30 days (LD50/30) after whole body radiation (WBI) in a test group of mice treated with said peptide at 72 hours after WBI and, testing which dose of radiation results in 50% mortality at 30 days (LD50/30) after whole body radiation (WBI) in a control group of mice treated only with the vehicle of said peptide at 72 hours after WBI and wherein the DRF is calculated by dividing the LD50/30 of the peptide-treated animals by the LD50/30 of the vehicle-treated animals.

(25) U.S. Patent Application Publication No. 2013/0035634 by Cappello, et al., which discloses a needle-free injection device having an outer housing and an inner housing. The inner housing is configured to receive a needle-free syringe in one end. In addition, the inner housing is movable within the outer housing between a syringe loading position and a firing position. The device also includes an activation button operatively associated with the inner and outer housings and a housing lock engaged by the activation button to prohibit movement of the inner housing from the syringe loading position to the firing position when the activation button is activated with the inner housing in the syringe loading position. Methods and apparatus for using, filing and operating the needle-free injection device are also disclosed.

(26) U.S. Patent Application Publication No. 2013/0150820 by Cappello, et al., which discloses a needle-free injection device suitable for delivering a therapeutic substance into the intradermal space of a patient. The needle-free injection device includes a main spring which can be compressed using one or more handles attached to the device to place the needle-free injection device into an armed configuration. Device embodiments may optionally include an injector tube and associated apparatus which may be moved relative to other device structures when the injector is pressed against the skin of a patient with sufficient force. The disclosed operational switches and release mechanisms cooperate to prevent injection unless the device is properly positioned for an injection. Needle-free injection systems and methods of operating a needle-free injection device are also disclosed.

(27) U.S. Patent Application Publication No. 2014/0005632 by Bingham, et al., which discloses a needle-less injector device for delivering a dose of fluid intradermally, subcutaneously or intramuscularly to an animal or human. The device includes an inner housing having opposed ends. A syringe is disposed in one end of the inner housing. The syringe includes a nozzle for delivering a dose of fluid held within the syringe. A plunger is movably disposed within the syringe. A spring powered hammer is movably disposed within the inner housing. The hammer cooperates with the plunger to drive the dose of medicament from the nozzle. An injection delivery spring for powering the hammer is positioned and compressed between the other end of the inner housing and the spring powered hammer. An outer housing slideably supports the inner housing. A skin tensioning spring is mounted between the inner housing and the outer housing, the skin tensioning spring biasing the nozzle of the syringe against the animal or human. A trigger mechanism is disposed in the outer housing, the trigger mechanism cooperating with the spring powered hammer to release the injection delivery spring, wherein the size of the injection delivery spring and the length of the hammer dictate the amount of dose delivered and whether the dose is delivered intradermally, subcutaneously or intramuscularly to an animal or human.

One embodiment is directed towards a prefilled cartridge for use with an injection device. The prefilled cartridge is configured to work with an injection device that is needle free or includes a needle. Any injection device configured to receive a cartridge may be utilized. The injection device may have a pen type shape and these devices are known in the art and described herein. In the embodiment, the prefilled cartridge includes a container having a first end configured to receive a cap and an open second end and a piston or plunger configured to be arranged within an interior portion of the container.

In one embodiment, the piston or plunger is operable to move from a first position to a second position, e.g., upon operation of an injection device when the cartridge is operably positioned within the injection device. This action of the injection device may be achieved by a mechanical action, electronic action, pneumatic action, magnetic action, air pressure action and combinations of the same. That is, a piston moves from a first position to a second position to engage with the piston or plunger of the prefilled cartridge.

The cartridge can also include a cap or other portion having a color code indicative of a predetermined concentration of at least one antigen contained within the cartridge. The cap also includes a seal, e.g., a self-healing seal permitting a needle or other device to puncture the seal and allowing it to be resealed upon the needle or other device.

One embodiment is directed towards a method of preparing an allergen extract for an immunotherapy treatment with a prefilled cartridge for use with an injection device. The method includes providing a first prefilled cartridge for use with the injection device, the prefilled cartridge includes a container having a first end configured to receive a cap and an open second end, a piston arranged within an interior portion of the container where the piston is operable to move from a first position to a second position, and a solution contained between the piston and the first end, the solution including a diluent for an allergenic extract. The method further includes adding at least one allergen extract to the prefilled cartridge to form the allergen extract for an immunotherapy treatment at first concentration. Optionally, additional steps may be performed to by adding a predetermined amount of the allergen extract at a first concentration in the prefilled cartridge to a second prefilled cartridge to form an allergen extract for an immunotherapy treatment at a second concentration.

One embodiment is directed towards a method of preparing an allergen extract for an immunotherapy treatment with a prefilled cartridge for use with an injection device. The method includes providing a prefilled cartridge including a solution having a diluent for an allergenic extract. Next, combining one or more allergenic extracts into a first container to form an allergenic extract concentrate and obtaining a predetermined volume of diluent in the prefilled cartridge. Next, forming an allergen extract for an immunotherapy treatment at a first concentration by combining a predetermined volume of the concentrate into the prefilled cartridge. Optionally, additional steps may be performed to by adding a predetermined amount of the allergen extract at a first concentration in the prefilled cartridge to a second prefilled cartridge to form an allergen extract for an immunotherapy treatment at a second concentration.

One embodiment is directed towards a method of preparing an allergen extract for immunotherapy treatment cartridge for use with an injection device. The method includes providing a prefilled cartridge containing where the prefilled cartridge is empty of any liquid. Next, combining one or more allergenic extract into a first container to form an allergenic extract concentrate and obtaining a predetermined volume of diluent in the prefilled cartridge. Next, forming the allergen extract for immunotherapy treatment by combining a predetermined volume of the concentrate into the prefilled cartridge. Optionally, additional steps may be performed to by adding a predetermined amount of the allergen extract at a first concentration in the prefilled cartridge to a second prefilled cartridge to form an allergen extract for an immunotherapy treatment at a second concentration.

One embodiment is directed towards a method of administering immunotherapy to a patient with an injection device and prefilled cartridge. The method includes providing the injection device and loading the prefilled cartridge into the injection device. The prefilled cartridge includes an efficacious amount of allergen extract for immunotherapy. Next, the injection is operated at a treatment situs of the patient to administer an efficacious dosage of the allergen extract.

One embodiment is directed towards a medical kit for immunotherapy. The medical kit may include an injection device and one or more prefilled cartridges include an allergen extract for immunotherapy and instructions for use. Optionally or alternatively, the medical kit for immunotherapy includes one or more prefilled cartridges comprising an allergen extract for immunotherapy or diluent without the allergen extract for immunotherapy.

In one embodiment, the injection device is a needle-free injector as described with reference to any patent and patent application publication herein including but not limited to U.S. Pat. Nos. 5,104,380; 7,547,293; 7,618,393; 7,699,802; 8,529,500 and U.S. Patent Application Publication Nos. 2007/0027428; 2013/0035634; 2013/0150820; and 2014/00632, each of which are hereby incorporated by reference as if fully set forth herein. Optionally, the cartridge includes a chamber as described with reference to any patent described herein including but not limited to U.S. Pat. Nos. 5,104,380; 7,547,293; 7,618,393; 7,699,802; 8,529,500 and U.S. Patent Application Publication Nos. 2007/0027428; 2013/0035634; 2013/0150820; and 2014/00632, each of which are hereby incorporated by reference as if fully set forth herein. Moreover, the geometry of the cartridge may be configured to fit within any injection device as known in the art. The cartridge may include any materials, e.g., glass, plastic, metal, alloy, composite materials, thermoplastic, tempered glass and combinations thereof. The cartridge may also be transparent, semitransparent or not transparent to light.

Alternately and/or optionally, the container includes a material selected from the group consisting of glass, plastic, thermoplastic, tempered glass, metal, alloy, composite, and combinations thereof.

Alternately and/or optionally, the cartridge, cap, plunger or piston, injection device and combinations of the same may include a radio frequency identification (RFID) tag or other device configured to contain or transmit data indicative of at least one of a concentration of at least one antigen, a patient identifier, a manufacturer of the antigen, a lot number, a lot date, a diluent identification, an antigen identifier and a manufacturer of the diluent, antigen or both. The RFID tag can be an active tag or passive tag.

Alternately and/or optionally, the cartridge, cap, plunger or piston, injection device and combinations of the same may include a one or more sensors configured to determine at least one of a temperature of the solution, a flow rate of the injection device in operation, a concentration of at least one antigen, a concentration of the injection diluent, a volume of the solution, a characteristic indicative of use of the injection device, a characteristic indicative of a time of use of the injection device, and a characteristic indicative of an angle of orientation of the injection device when used. The sensors may further communicate wirelessly with a receiver/transmitter as known in the art, e.g., a wireless communication unit configured to output information from the one or more sensors Alternately and/or optionally, the cartridge, cap, plunger or piston, injection device and combinations of the same may include a light emitting diode or light source. The light emitting diode or light source is configured to emit a colored light indicative of one or more of a concentration of the solution, temperature of the solution, predetermined time of treatment, volume of solution, and incorrectly loading of the cartridge into the injection device.

Alternately and/or optionally, the cartridge, cap, plunger or piston, injection device and combinations of the same may include a power source. The power source can include a battery configured to be inductively or remotely charged.

In one embodiment, the diluent include broadest definition. In a preferred embodiment, the diluent includes one of glycerin, Phenol, saline, and acrylonitrile butadiene styrene (ABS). In another embodiment, the diluent can include 0.9% NaCl, 0.03% human albumin, and 0.4% phenol in water. In yet another embodiment, the diluent can include about 50% glycerin and phenol. In still yet another embodiment, the diluent includes 0.4% phenol and/or saline. In yet another embodiment, the diluent includes 0.03% HSA, 0.4% phenol, and saline.

In one embodiment, the cartridge includes an allergenic extract configured to elicit an immune response. Optionally, the allergen extract includes one or more of a tree pollen vector allergen, grass pollen vector allergen, weed pollen vector allergen, mold vector allergen and other vector allergen.

In one embodiment, the increased concentration utilized in immunotherapy is based on a predetermined algorithm or mathematical function, e.g., a linear line with a positive slope, for a predetermined amount of time, e.g., a six week basis. In a preferred embodiment, the immunotherapy treatment includes administering two shots per week for six weeks at a first concentration, e.g., 5,000 dilution for six weeks. The volume of each shot changes as a linear function, e.g., 0.03 mL increments. That is, the first shot, week one, concentration of 5,000 dilution would be at a starting amount, e.g., in a range from about 0.02 mL to about 0.04. The second shot that week would be adjusted by about 0.03 mL with the same dilution amount. The maximum volume would be in week six and would not exceed 0.39 mL. Moreover, the shots should be given at least 48 hours apart in each week. It is noted this would be considered a first round of treatment at the first concentration of allergen extract. The treatments may be provided by either a provider or a patient with an injection device. In addition, it is understood that this treatment may be adjusted based on adverse reactions from the patients. In one embodiment, the method is adjusted by a predetermined criteria by reducing the volume to one or more previously successfully administered treatment without adverse reactions.

By way of example, one embodiment is directed towards a six week treatment of increased dosage or volume also called a ramp over a predetermined time frame, which may be administered with a prefilled cartridge utilizing an injection device. Optionally, a pretreatment prior to the treatment set being is utilized in order to reduce adverse reactions, preferably, the pretreatment is configured as one injection at a dosage or volume configured to prevent any next increase from being higher than fifty percent. In preferred embodiment, the dosage or volume of the pretreatment is in a range from about 0.01 ml to about 0.04 ml, and more preferably about 0.04 ml.

Ramping may be a predetermined time frame from about 1 week to 6 weeks or greater, preferably 6 weeks. In one ramping embodiment, a pretreatment injection of about 0.04 ml was administered with the injection device or other instrument and prefilled cartridge. Next, the ramp started at a 1:5,000 dilution according to the following schedule could be used as follows: Week 1: shot 1—0.06 mL, 5,000 dilution, shot 2—0.09 mL, 5,000 dilution; Week 2: shot 1—0.12 mL, 5,000 dilution, shot 2—0.15 mL, 5,000 dilution; Week 3: shot 1—0.18 mL, 5,000 dilution, shot 2—0.21 mL, 5,000 dilution; Week 4: shot 1—0.24 mL, 5,000 dilution, shot 2—0.27 mL, 5,000 dilution; Week 5: shot 1—0.30 mL, 5,000 dilution, shot 2—0.33 mL, 5,000 dilution; Week 6: shot 1—0.36 mL, 5,000 dilution, shot 2—0.39 mL, 5,000 dilution. Next, the concentration is increased to a mixture with a concentration of 1:500 vol/vol or 500 dilution and a six week treatment set is repeated, however, the starting point is not 0.03 mL, but 0.06 mL, therefore the ending point in week six is 0.39 mL. This is repeated for the rest of the concentrations in six week increments until the 1.5 vol/vol or 5 dilution is given in the six week ramp treatment. Next a maintenance schedule is given for about six months or longer. The maintenance schedule is linear and two shots per week at 0.30 mL to 0.39 mL are given. There is no change in volume from week to week or concentration from week to week or shot to shot. The amount of volume change between shots and durations of schedules is dependent on the efficacy and safety of the immunotherapy and may be adjusted to stay within the efficacy and safety bounds.

Reference will now be made in detail to an embodiment of the present invention, example of which is illustrated in the accompanying drawings.

FIG. 1 illustrates a perspective view of a prefilled cartridge.

Referring to FIG. 1, the prefilled cartridge is generally depicted with reference to number 100. The prefilled cartridge 100 can be utilized with a delivery apparatus, e.g., an injection device or other automatic delivery system. The cartridge 100 is configured for a single disposable use and is also configured to receive an additive of liquids or gels, e.g., a diluent for an allergenic extract, an allergenic extract, and combinations of the same.

In this embodiment, the prefilled cartridge 100 is utilized for immunotherapy. The cartridge 100 includes a stopper or plunger 102 or piston and a cap 104. The cap 104 includes seal 106 which is configured to be self-healing and is made of a thermoplastic material, e.g., an integral cap and seal such as a rubber disk. The self-healing of the seal allows for a needle to be inserted through the seal to add and subtract fluid or gel in the cartridge 100. Upon removal of the needle the seal 106 is sealed automatically with the self-healing material to prevent fluid from escaping. Optionally, the seal 106 may include more than one layer to enhance the self-healing ability, e.g., a dual layer seal including a first layer resistant to chemical and a second layer to aid in sealing or self-healing after a predetermined used, e.g., 5 or more uses or penetrations. The first layer includes at least one of a thermoplastic material, polymer material, and combinations of the same and the second layer includes thermoplastic material, polymer material, and combinations of the same. Optionally, the seal may include additional layers for other functionality or performance criteria. In one embodiment, the seal 106 is a hermetic seal. Optionally, the seal may be semi-permeable such that it is configured to prevent fluid from exiting the cartridge, but allows a gas to pass through at a pressure greater than atmospheric pressure. This type of semi-permeable seal may be useful in adding and removing fluids to the prefilled cartridge 100. For example, with reference to FIG. 3 disclosed herein, the volume of the prefilled cartridge is configured to work the injection device. In a preferred embodiment, the volume is about 3.0 ml. Alternatively or optionally, the piston 102 may include one or more sensors 107 and a power source 105 integral with the piston 102. Moreover, the sensor 107 may be configured as described herein and also be an RFID tag.

Figure 2:
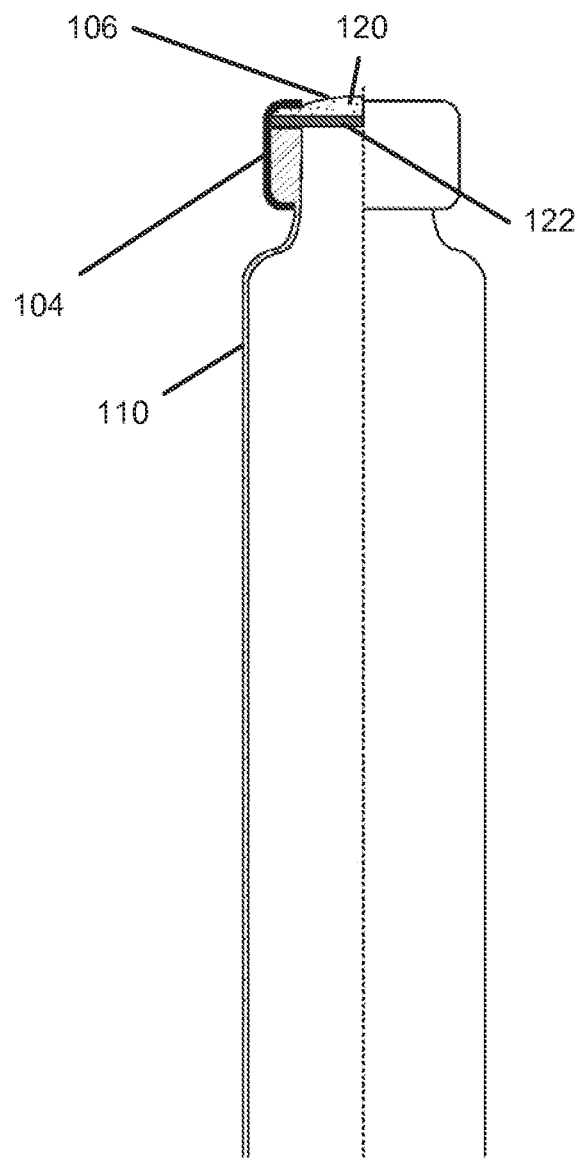
FIG. 2 illustrates a perspective view of a cap according to an embodiment of the invention.

Referring now to FIG. 2, which illustrates a cross-sectional view of an integral cap according to an embodiment of the invention. The cap 104 in this embodiment includes a dual layer seal 106. The first layer 120 includes at least one of a thermoplastic material, polymer material, and combinations of the same and the second layer 122 includes thermoplastic material, polymer material, and combinations of the same. One end 108 of the cartridge 100 is open and the other end may also be open prior to applying the cap. Moreover, the cap may be integrated with the end of the cartridge. In such a case, the end 112 would not include a cap, but would have a self-healing plug to close the end. The plug (not shown) could be made with thermoplastic material.

The cap may be a pressure fit cap, a threaded cap, or include another fastening mechanism and combinations of the same configured to hold it place. The cap may be constructed from a metal material, alloy material, plastic material, composite material, and combinations of the same. In a preferred embodiment, the cap includes an aluminum material. Optionally, the aluminum material is color coated.

Referring again to FIG. 1, the stopper or plunger 102 is operationally coupled to a plunger or piston of the pen and the plunger 102 is configured to move from a first position to second position upon application of linear force to the stopper 102. The stopper 102 may be configured to be removable from the end of the cartridge 100. This removability may be advantageous for prefilling the cartridge with the desired liquid. Moreover, the stopper 102 can be constructed of thermoplastic material and is configured to provide a fluid seal to the liquid between the cap 106 and the stopper 102. In one embodiment, the stopper 102 may be self-sealable similar to the seal 106 as described herein with respect to the seal 106, thereby allowing a needle to penetrate the stopper 102 and permit the addition and removal of liquid in the cartridge 100.

In a preferred embodiment, the cartridge includes a glass material, e.g., borosilicate glass. Other materials may also be used, e.g., metal, alloy, composite, glass and combinations of the same. Optionally, the edges of the cartridge are buffered to remove any type of sharp edges. Moreover, a circular protective ring (not shown) can be placed on the edges to prevent any exposure to sharp edges. In addition, the interior walls 110 of the cartridge may be coated with an anti-frictional material, e.g., silicon, PTFE and/or the like. For example, one or more internal surface may include a hydrophilic coating that substantially reduces or eliminates accumulation of medication deposits as described in U.S. Pat. No. 6,443,942, which is hereby incorporated by reference. Other types of coatings may be used such a hydrophobic coating and/or siliconization. In one embodiment, the at least a portion of an interior of the cartridge is treated with a material that is a lubricant, a hydrophobic coating or hydrophilic coating that is resistant to corrosive or other negative effects from phenol and/or antigens. In addition, the prefilled cartridge is sterilized as known in the art.

The cap 104, plug, and/or cartridge 100 may be color coded with any color. In one embodiment, the color coding includes a red cap, a yellow cap, a green cap, a blue cap and a silver cap to indicate predetermined concentrations of extracts in the container. The color coding may be achieved with a plastic covering or integrated fully with the cap 104. The cap may include a solid color or a line of color or other mechanism or element configured to be indicative of a concentration of allergen extract. The color coding may also be achieved with a second plastic cap (not shown) that is coded cap and configured to fit around an existing cap on the prefilled cartridge.

In one embodiment, the cap uses predetermined colors to indicate a specific concentration. For example, the cap colors chosen may be red, yellow, blue, green, and silver. A red cap is indicative of a concentrate 1:1 vol/vol, a yellow cap is indicative of a 10 fold dilution 1:10 vol/vol, a blue cap is indicative of a 1:100 vol/vol, a green is indicative of a 1000 fold dilution 1:1,000 vol/vol, and a silver cap is indicative of a 10,000 fold dilution 1:10,000 vol/vol. Of course in other embodiments other cap colors may by indicative of other concentrations, e.g., a red cap may be indicative of a concentrate 1:1 vol/vol, a yellow cap is indicative of a 5 fold dilution 1:5 vol/vol, a blue cap is indicative of a 50 fold dilution 1:50 vol/vol; a green cap is indicative of a 500 fold dilution 1:500 vol/vol; and a silver cap is indicative of a 5,000 fold dilution 1:5,000 vol/vol.

Also, the cap colors may simply be indicative of a hierarchy of concentrations, e.g., from more to less and vice versa. In one embodiment, there are five colors, red, yellow, blue, green and silver and the hierarchy of concentration from higher to lower is from red to silver where red is the highest concentration and silver is the lowest concentration.

The cartridge may be prefilled with a diluent for an allergenic extract, allergen, antigen, allergen extract and combination of the same. An allergen is any substance that is configured to elicit an immune response. The extracts are used in an immunotherapy treatment include one more allergens also called an antigen configured to elicit an immune response. In a preferred embodiment, the allergens are classified into broad categories based on a transmission or other functional characteristics of the allergens. For example, the first category is called a vector group, and includes a pollen vector group, an animal vector group, a control vector group and an environment vector group.

In addition, these vector groups can have a further classification of allergens into sub-vector groups below each vector group. For example, the pollen vector group includes a tree sub-vector group, a grass sub-vector group, a weed sub-vector group, a plant sub-vector group and other pollen transmitting sub-vector groups. The animal vector group includes an indoor animal sub-vector group and an outdoor animal sub-vector group. The control vector group includes a saline control sub-vector group and histamine control sub-vector group. The environmental vector group includes a mold sub-vector group and cockroach allergens. Optionally and/or alternatively, the allergens within each sub-vector group may be further classified into one or more of seasons, amount of pollen produced per a predetermined time of one or more plant, tree, weed, or grass associated with each a specific vector group, sub-vector group or both, a cross-reactivity designation of one or more antigens in each sub-vector group, a frequency designation of one or more plant, tree, weed, or grass associated with each a specific vector group, sub-vector group or both per a predetermined area, and a meteorological factors associated with one or more plant, tree, weed, or grass associated with each a specific vector group, sub-vector group.

In one embodiment, the tree sub-vector group includes one or more allergens, e.g., an Acacia, Golden (*Acacia longifolia*); Alder, Red (*alnus rubra (oregona)*); Ash, White (*Faxinus grandifolia*); Beech, American (*Fagus grandifolia*); Birch Mix (Paper, River/Red & White Birch); Boxelder/Maple Mix (Boxelder, Hard Maple & Red Maple); Cedar, Mountain (*Jumperus ashei*); Cedar, Red (*Juniperus virginiana*); Cottonwood, Common (*Populus deltoides*); Cypress, Ariz. (*Curpressus arizonica*); Cypress, Bald (*Taxodium distichum*); Elm, American (*Ulmus americana*); Elm, Chinese (*Ulmus parvifolia*); Eucalyptus/Blue Gum (*Eucalyptus globulus*); Gum, Sweet (*Liquidambar styraciflua*); Hackberry (*Celtis occidentalis*); Hickory, Shagbark (*Carya ovata*); Linden/Basswood (*Tilia americana*); Maple, Hard/Sugar (*Acer saccharum*); Mesquite (*Prosopis juliflora (glan-*

*dulosa*)); Mulberry Mix (Red & White Mulberry); Oak, Red (*Quercus rubra*); Oak Mix (Red, Virginia Live & White Oak); Olive Tree (*Olea europaea*); Bottlebrush Tree (*Callistemon citrinus*); Melaleuca (*Melaleuca quinquenervia*); Palm, Queen (*Cocos plumose*); Pecan Tree (*Carya pecan* (*illinoensis*); Pepper Tree, Calif. (*Schinus molle*); Pine Mix (Lodgepole & Western Yellow Pine); Privet, Common (*Lingustrum vulgare*); Russian Olive (*Elaeagnus angustifolia*); Sycamore, American (*Platanus occidentalis*); Tree Mix (Pecan, Maple, Oak, American Sycamore, Black Willow); Tree Mix (White Ash, American Beech, Birch, Black Walnut, Common Cottonwood, American Elm); Tree Mix (White Ash, American Beech, River/Red Birch, Black Walnut, Common Cottonwood, American Elm, Shagbark Hickory, Hard Maple, Red Oak, American Sycamore, Black Willow); Walnut, Black (*Juglans nigra*); Willow, Black (*Salix nigra*); and the like.

There are a number of different allergens configured in the grass sub-vector group. In one embodiment, the allergens in this grass sub-vector group include one or more of Acacia, Bahia Grass (*Paspalum notatum*); Bermuda Grass (*Cynodon dactylon*); Bluegrass, Ky. (*Poa pratensis*); Brome, Smooth (*Bromus inermis*); Corn, Cultivated (*Zea mays*); Fescue, Meadow (*Festuca elation (pratensis*); Grass Mix (Kentucky Bluegrass, Orchard, Redtop, Timothy); Grass Mix (Kentucky Bluegrass, Orchard, Redtop, Timothy, Sweet Vernalgrass); Grass Mix (Kentucky Bluegrass, Orchard, Redtop, Timothy, Sweet Vernalgrass, Meadow Fescue, Perennial Ryegrass); Grass Mix (Kentucky Bluegrass, Bermuda, Johnson, Redtop, Timothy); Johnson Grass (*Sorghum halepense*); Oats, Common Cultivated (*Avena sativa*); Orchard Grass (*Dactylis glomerate*); Redtop (*Agrostis gigantea (alba*)); Ryegrass, Perennial (*Lolium perenne*); Southern Grass Mix (Kentucky Bluegrass, Orchard, Redtop, Timothy, Sweet Vernalgrass, Bermuda, Johnson); Sweet Vernalgrass (*Anthoxanthum odoratum*); Timothy (*Phleum pratense*); and the like.

There are a number of different allergens configured in the weed sub-vector group. In one embodiment, the allergens the weed sub-vector group include one or more of Acacia, Careless Weed (*Amaranthus palmeri*); Careless/Pigweed (Careless Weed & Rough Redroot Pigweed); Cocklebur, Common (*Xanthium strumarium*); Dock/Sorrel Mix (Yellow Dock & Sheep Sorrel); Goldenrod (*Solidago canadensis*); Kochia (*Kochia scoparia*); Lamb's Quarters (*Chenopodium album*); Marshelder/Poverty Mix (Burwee, Povertyweed & True Marshelder); Nettle (*Urtica dioica*); Dog Fennel, Eastern (*Eupatorium capillifolium*); Pigwee, Rough Redroot (*Amaranthus retroflexus*); Plantain, English (*Plantago lanceolata*); Ragweed, Giant (*Ambrosia trifida*); Ragweed, Short (*Ambrosia artemisilifolia*); Ragweed, Western (*Ambrosia psilostachya*); Ragweed Mix (Giant & Short Ragweed); Ragweed (Giant, Short & Western Ragweed); Russian Thistle (*Salsola kali*); Sagebrush, Mugwort (*Artemisia vulgaris Heterophylla (douglasiana*)); Scale, Wing (*Atriplex canescens*); Sheep Sorrel (*Rumex acetosella*); Weed Mix 2630 (Common Cocklebur, Lamb's Quarters, Rough Redroot Pigweed, Dock/Sorrel); and the like.

There are a number of different allergens configured in the mold sub-vector group. In one embodiment, the allergens the mold sub-vector group include one or more of Alternaria-Hormodendrum Mix (*Alternaria tenuis, Hormodendrum cladosporioides*); *Alternaria tenuis; Aspergillus fumigatus; Aspergillus niger; Botrytis cinerea; Candida albicans; Cephalosporium acremonium; Curvularia spicifera; Epicoccum nigrum; Epidermophyton floccosum; Fusarium vasinfectum; Helminthosporium interseminatum; Hormodendrum cladosporioides; Mucor racemosus;* Penicillium Mix (*p. digitatum, expansum, glaucum, roseum, notatum*); *Penicillium notatum; Phoma herbarum; Pullularia pullulans; Rhizopus nigricans; Stemphylium botryosum; Trichopyton* Mix (*T. tonsurans, rubrum, mentagrophytes*); Mold Mix (*Alternaria tenuis*, Aspergillus Mix (*A. fumigatus, nidulans, niger, terreus*), *Hormodendrum cladosporioides,* Penicillium Mix (*P. digitatum, expansum, glaucum, notatum, roseum*); Mold Mix *Alternaria tenuis,* Aspergillus Mix (*A. fumigatus, nidulans, niger, terreus*), *Fusarium vasinfectum, Helminthosporium interseminatum, Hormodendrum cladosporioides, Mucor racemosus,* Penicillium Mix (*P. digitatum, expansum, glaucum, notatum, roseum*), *Phoma herbarum, Pullularia pullulans, Rhizopus nigricans*; and the like.

There are a number of different allergens configured in the animal vector group. In one embodiment, the allergens in this animal vector includes one or more of Dog Hair and Dander (Mixed breeds); Feather Mix (Chicken, Duck and Goose); Guinea Pig Hair and Dander; Cat Pelt; Cat Hair; Cattle Hair and Dander; Horse Hair and Dander; House Dust Mix (Feather and Mattress dust), DP Mite and DF Mite (even though not an animal); and the like.

There are a number of different allergens configured in the mold sub-vector group. In one embodiment, the allergens in this mold sub-vector group includes one or more of *Alternaria tenuis; Aspergillus fumigatus; Aspergillus niger; Candida albicans; Cephalosporium acremonium; Curvularia spicifera; Epidermophyton floccosum; Fusarium vasinfectum; Mucor racemosus; Hormodendrum; Helminthosporum;* Penicillium Mix; *Phoma herbarum; Pullularia pullulans; Rhizopus nigricans; Stemphylium botryosum;* Trichopylton Mix; *Epicoccum nigrum; Botrytis cinerea*, cockroach mix (even though not a mold), and the like.

In another embodiment, allergen extract treatment sets are made from prefilled cartridges or with empty cartridges. In a preferred embodiment, the prefilled cartridges include a diluent for an allergenic extract.

In one embodiment, a patient treatment set may be formed at a provider's office or other predetermined location. The treatment set is configured to provide a predetermined course of immunotherapy to a patient for a predetermined amount of time. In a preferred embodiment, five allergen extracts of predetermined concentrations are combined to provide the predetermined course of allergy treatments. The number of different allergen extracts may vary, e.g., 1, 2, 3, 4, 5, 6, 7, 8, 9, 10, 11, 12, 13, 14, 15, 16, 17, 18, 19, 20 or more. The selection of these allergen extracts are as desired by the clinician, patient, other provider and any combination of the same.

In this embodiment, an immunotherapy treatment set is formed. Allergen extracts are combined into a single container, e.g., five or more different allergen extracts are combined into one container. The container may be 10 mL or greater. In container now contains a concentrate or immunotherapy concentrate. The container may also be a cartridge of adequate volume. In this embodiment, the concentration of each of the five different allergen extracts is similar such that the effective concentration for treatment of each of the five different allergen extracts is similar. This concentrate is now 1:1 vol/vol and is utilized to create the immunotherapy treatment set. This concentrate is now a mixture of all of the five or more different allergen extracts into one container.

Next, a second container, e.g. a 10 mL container, containing 8 mL of a diluent for an allergenic extract is mixed with 2 mL of the concentrate (1:1 vol/vol) to create a 1:5 vol/vol mixture (5 dilution). Next, a third container, e.g., a 10 mL container, containing 9 mL of diluent for an allergenic extract is mixed with 1 mL of the 1:5 vol/vol mixture (5 dilution) to create a 1:50 vol/vol mixture (50 dilution). Next, a fourth container, e.g., a 10 mL container, containing 9 mL of diluent for an allergenic extract is mixed with 1 mL of the of 1:50 vol/vol mixture (50 dilution) to create a 1:500 vol/vol mixture (500 dilution). Next, a fifth container, e.g., a 10 mL container, containing 9 mL of diluent for an allergenic extract is mixed with 1 mL of the 1:500 vol/vol mixture (500 dilution) to create a 1:5,000 vol/vol mixture (5,000 dilution).

In this embodiment, the different dilutions can now be transferred to empty cartridges to create an immunotherapy treatment for use with an injection device, e.g., an injection pen. A 1:5 vol/vol mixture (5 dilution) treatment is made by transferring the 1:5 vol/vol mixture into an empty cartridge, e.g., a 10 mL cartridge. This cartridge is labeled with a cap having a color, e.g., yellow, that is preexisting or added to the cap to indicate the concentration of the immunotherapy. Moreover, a label, e.g., an RFID label (active or passive), may be added to the cartridge containing the mixture to indicate one or more of the concentration, specific allergen extracts in the mixture, age of the mixture, origin of the allergen extracts, and other parameters. This can be repeated to obtain multiple 1:5 vol/vol mixture treatments.

A 1:50 vol/vol mixture (50 dilution) treatment is made by transferring the 1:50 vol/vol mixture into an empty cartridge, e.g., a 10 mL cartridge. A 1:500 vol/vol mixture (500 dilution) treatment is made by transferring the 1:5 vol/vol mixture into an empty cartridge, e.g., a 10 mL cartridge. A 1:5,000 vol/vol mixture (5,000 dilution) treatment is made by transferring the 1:5,000 vol/vol mixture into an empty cartridge, e.g., 10 mL cartridge. These cartridges are labeled to indicate the concentration of the mixture, e.g., a preexisting blue cap or added cap can be used for the 1:50 vol/vol mixture, a preexisting green cap or added cap can be used for the 1:500 vol/vol mixture, and a preexisting silver cap or added cap can be used form the 1:5,000 vol/vol mixture. Moreover, an RFID label as described herein can be added to the cartridges. This method can be repeated to obtain multiple mixture treatments.

Next these labeled cartridges are placed in a treatment box or container. In a preferred embodiment, the box or container is configured to hold two or more cartridges of each treatment dilution concentration and all treatment dilutions are in one container. This treatment set is used by a patient for immunotherapy and may be called an immunotherapy treatment set. In a preferred embodiment, these treatments sets are formed in a medical office, hospital or other medical center.

Figure 3:
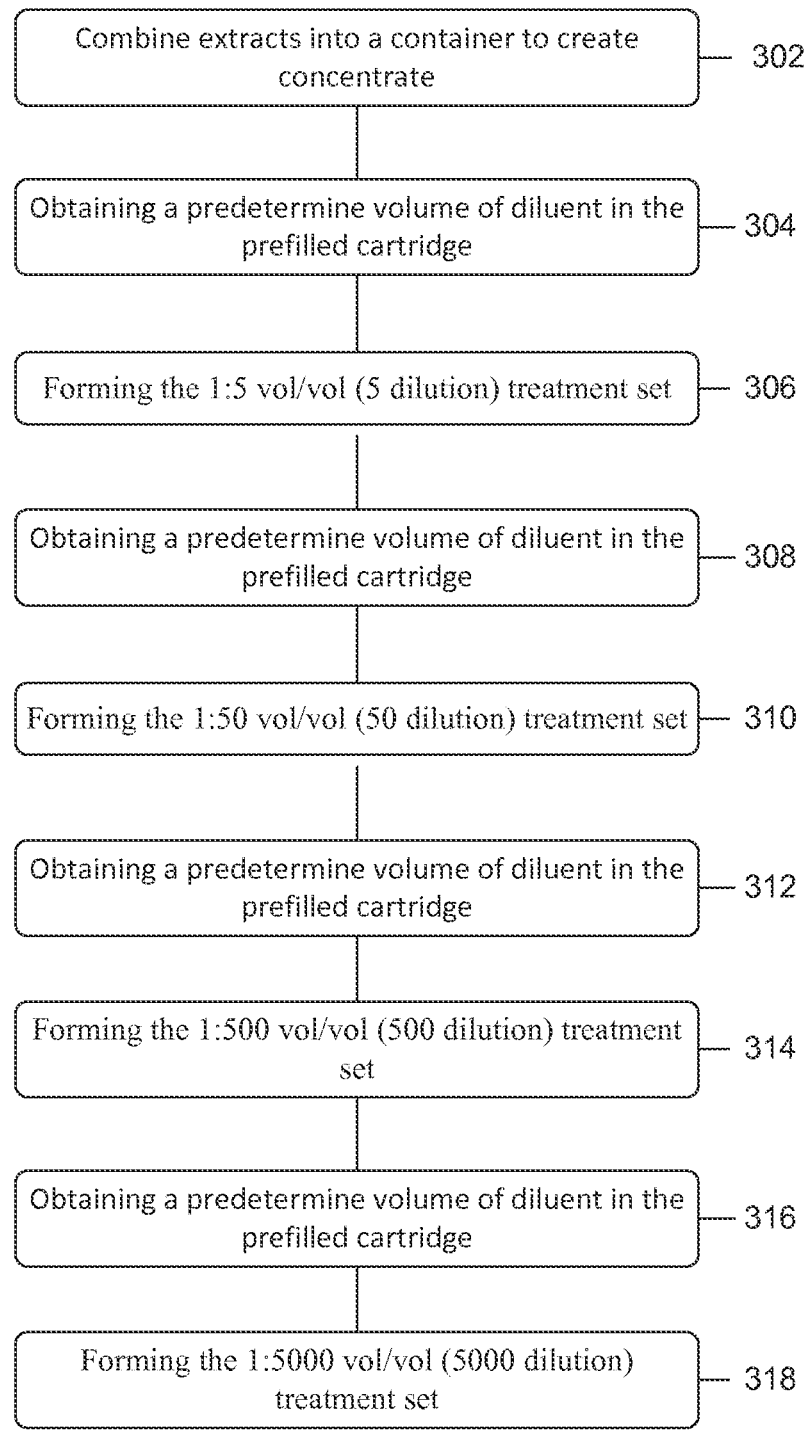
FIG. 3 illustrates a method of preparing an immunotherapy treatment set with prefilled cartridges according to an embodiment of the invention.

FIG. 3 illustrates a method of preparing an immunotherapy treatment set with prefilled cartridges according to an embodiment of the invention.

The treatment set is configured for treating a patient for six weeks at each treatment concentration. In this embodiment, the treatment set includes two immunotherapy prefilled cartridges at each of the following concentrations is indicative of a 5 fold dilution 1:5 vol/vol, a 50 fold dilution 1:50 vol/vol, a 500 fold dilution 1:500 vol/vol, and a 5,000 fold dilution 1:5,000 vol/vol. The prefilled cartridges are color coded with as described herein.

Referring to FIG. 3 in step 302 allergen extracts are combined into a single container, e.g., five or more predetermined allergen extracts are combined into one container. The container may be 10 mL or greater. The container now contains a concentrate or immunotherapy concentrate of the predetermined allergen extracts. In this embodiment, the concentration of each of the five different allergen extracts is similar such that the effective concentration for treatment of each of the five different allergen extracts is similar. This concentrate is now 1:1 vol/vol and is utilized to create the immunotherapy treatment set. This concentrate is now a mixture of all of the five or more different allergen extracts into one container.

In step 304, a predetermined amount of diluent is obtained in the prefilled cartridge. This may be accomplished by either adding or subtracting diluent to the prefilled cartridge to obtain the predetermined volume of diluent. Specifically, the prefilled cartridge may include 3.0 ml of diluent, so 0.3 ml is removed to obtain a 2.7 ml volume of diluent in the prefilled cartridge. In step 306, forming the 1:5 vol/vol (5 dilution) can be accomplished by mixing 0.3 ml of the concentrate (from Step 302) into the prefilled cartridge containing 2.7 mL (from Step 304). Steps 304 and 306 are repeated to obtain a second prefilled cartridge at 1:5 vol/vol mixture (5 dilution) and may be repeated additional times as well. These prefilled cartridges are labeled as described herein.

In step 308, a predetermined amount of diluent is obtained in the prefilled cartridge. This may be accomplished by either adding or subtracting diluent to the prefilled cartridge to obtain the predetermined volume of diluent. Specifically, the prefilled cartridge may include 3.0 ml of diluent, so 0.3 ml is removed to obtain a 2.7 ml volume of diluent in the prefilled cartridge. In step 310, forming the 1:50 vol/vol (50 dilution) can be accomplished by mixing 0.3 ml of the 1:5 vol/vol (5 dilution) concentrate (from Step 306) into the prefilled cartridge containing 2.7 mL (from Step 308). Steps 308 and 310 are repeated to obtain a second prefilled cartridge at 1:50 vol/vol mixture (50 dilution) and may be repeated additional times as well. These prefilled cartridges are labeled as described herein.

In step 312, a predetermined amount of diluent is obtained in the prefilled cartridge. This may be accomplished by either adding or subtracting diluent to the prefilled cartridge to obtain the predetermined volume of diluent. Specifically, the prefilled cartridge may include 3.0 ml of diluent, so 0.3 ml is removed to obtain a 2.7 ml volume of diluent in the prefilled cartridge. In step 314, forming the 1:500 vol/vol (500 dilution) can be accomplished by mixing 0.3 ml of the 1:50 vol/vol (50 dilution) concentrate (from Step 310) into the prefilled cartridge containing 2.7 mL (from Step 312). Steps 312 and 314 are repeated to obtain a second prefilled cartridge at 1:500 vol/vol mixture (500 dilution) and may be repeated additional times as well. These prefilled cartridges are labeled as described herein.

In step 316, a predetermined amount of diluent is obtained in the prefilled cartridge. This may be accomplished by either adding or subtracting diluent to the prefilled cartridge to obtain the predetermined volume of diluent. Specifically, the prefilled cartridge may include 3.0 ml of diluent, so 0.3 ml is removed to obtain a 2.7 ml volume of diluent in the prefilled cartridge. In step 318, forming the 1:5,000 vol/vol (5,000 dilution) can be accomplished by mixing 0.3 ml of the 1:500 vol/vol (500 dilution) concentrate (from Step 314) into the prefilled cartridge containing 2.7 mL (from Step 316). Steps 316 and 318 are repeated to obtain a second prefilled cartridge at 1:5,000 vol/vol mixture (5,000 dilution) and may be repeated additional times as well. These prefilled cartridges are labeled as described herein.

The treatment set includes two immunotherapy prefilled cartridges at each of the following concentrations is indicative of a 5 fold dilution 1:5 vol/vol, a 50 fold dilution 1:50 vol/vol, a 500 fold dilution 1:500 vol/vol, and a 5,000 fold dilution 1:5,000 vol/vol. The prefilled cartridges are color coded with as described herein. Optionally, more or less cartridges can be utilized. In addition, the treatment set may also include instructions for home use immunotherapy and an injection pen.

In the methods described herein a needle and syringe or other device may be used to transfer liquid from one container (prefilled cartridge) to another container. Moreover, caps on the prefilled cartridges may be removable or non-removable. In a preferred embodiment, the needle is inserted through a resealable membrane on the cap of the cartridge to add or subtract diluent for an allergenic extract or allergen extract. After removing the needle the resealable membrane closes automatically. Resealable and self-healing are used interchangeably herein.

Figure 4:
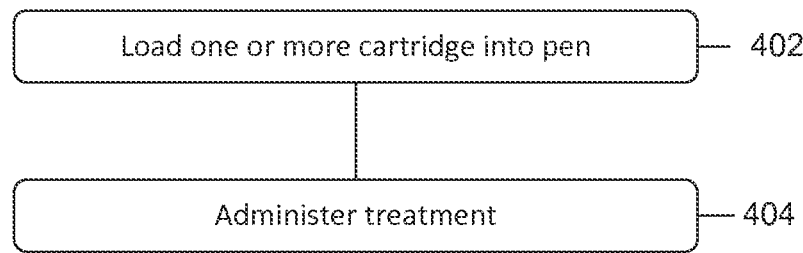
FIG. 4 illustrates a method of administering immunotherapy to a patient with an injection device and prefilled cartridge.

FIG. 4 illustrates a method of administering immunotherapy to a patient with an injection pen and prefilled cartridge.

In step 402, a cartridge with an immunotherapy treatment is loaded into the pen. In step 404, the pen is utilized to administer an efficacious amount of allergen extract preferably in a range from about 0.4 ml to about 0.27 ml. For example, using an injection pen to administer to the patient an effective dosage of an allergen extract.

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of preparing an allergy treatment with a prefilled cartridge for use with an injection device, comprising the steps of:
providing the prefilled cartridge including a solution comprising a first predetermined volume of diluent for an allergenic extract, wherein the prefilled cartridge comprises a first end and a second end, the first end is closed with a cap including a portion arranged within an interior of the cap, the portion of the cap including a self-healing material configured to allow a needle to be inserted through the self-healing material in order to add and subtract fluid to the prefilled cartridge and the second end being open, the prefilled cartridge further comprises a piston arranged within an interior of the prefilled cartridge configured to move from a first position to a second position upon application of an external force provided by the injection device;
providing one or more allergenic extracts;
providing a first container;
combining the one or more allergenic extracts into the first container to form an allergenic extract concentrate;
obtaining a predetermined volume of the allergenic extract concentrate; and
forming the allergy treatment into the prefilled cartridge at a first concentration by adding the predetermined volume of the allergenic extract concentrate into the prefilled cartridge containing the first predetermined volume of diluent to form the allergy treatment in the prefilled cartridge at a first concentration.

2. The method of claim 1, further comprising the steps of:
providing a second prefilled cartridge comprising a solution comprising a second predetermined volume of diluent for the allergenic extract, wherein the first predetermined volume is different than the second predetermined volume;
obtaining a second predetermined volume of the allergenic extract concentrate; and
forming an allergy treatment at a second concentration different than the first concentration, by adding the second predetermined volume of the allergen extract concentrate into the second prefilled cartridge containing the second predetermined volume of diluent to form the allergy treatment cartridge at the second concentration wherein the second concentration is different than the first concentration.

3. The method of claim 1, wherein the diluent comprises at least one of glycerin, Phenol, saline, and acrylonitrile butadiene styrene (ABS).

4. The method of claim 1, wherein the diluent comprises 0.4% phenol.

5. The method of claim 1, wherein the one or more allergenic extracts is configured to elicit an immune response.

6. The method of claim 1, wherein the one or more allergenic extracts comprises an extract selected from the group consisting of an aqueous form, a glycerinated form, a lyophilized form, acetone precipitated form, alum precipitated form, phenol precipitated form and combinations thereof.

7. The method of claim 1, wherein the one or more allergenic extracts comprising at least one antigen.

8. The method of claim 1, wherein the one or more allergenic extracts includes one or more of a tree pollen vector allergen, grass pollen vector allergen, weed pollen vector allergen, mold vector allergen and other vector allergen.

9. The method of claim 1, wherein the injection device comprises a needleless injection device.

10. The method of claim 1, wherein the injection device comprises a needle for injection.

11. The method of claim 1, wherein the injection device comprises a pen type injection device.

12. A method of preparing an allergy treatment for use with an injection device, comprising the steps of:

providing a cartridge, wherein the cartridge is empty of any liquid, wherein the cartridge comprises a first end and a second end, the first end is closed with a cap including a portion arranged within an interior of the cap, the portion of the cap including a self-healing material configured to allow a needle to be inserted through the self-healing material in order to add and subtract fluid to the cartridge and the second end being open, the cartridge further comprises a piston arranged within an interior of the cartridge configured to move from a first position to a second position upon application of an external force provided by the injection device;

providing one or more allergenic extracts;

providing a first container;

combining the one or more allergenic extracts into the first container to form an allergenic extract concentrate;

obtaining a predetermined volume of diluent;

adding the predetermined volume of the diluent to the cartridge with a needle through the self-healing material;

obtaining a predetermined volume of the allergenic extract concentrate; and forming the allergy treatment by combining the predetermined volume of the allergenic extract concentrate into the cartridge containing the predetermined volume of the diluent with a needle through the self-healing material to form the allergy treatment at a first concentration.

13. A method of administering an allergy treatment to a patient with an injection device and prefilled cartridge containing the allergy treatment at a first concentration, comprising the steps of:

providing the injection device;

loading the prefilled cartridge into the injection device, wherein the prefilled cartridge comprises the allergy treatment at the first concentration for treating allergies, wherein the prefilled cartridge comprises a first end and a second end, the first end is closed with a cap including a portion arranged within an interior of the cap, the portion of the cap including a self-healing material configured to allow a needle to be inserted through the self-healing material in order to add and subtract fluid to the prefilled cartridge and the second end being open, the prefilled cartridge further comprises a piston arranged within an interior of the prefilled cartridge configured to move from a first position to a second position upon application of an external force provided by the injection device; and using the injection device at treatment situs of the patient to administer an efficacious dosage of the allergy treatment.

14. The method of claim 13, wherein the using the injection device step is done by the patient.

15. The method of claim 13, wherein the using the injection device step is done by a medical provider.

* * * * *